United States Patent
Schwab et al.

(10) Patent No.: US 9,133,165 B2
(45) Date of Patent: Sep. 15, 2015

(54) SULFONIC ACID SALTS OF HETEROCYCLYLAMIDE-SUBSTITUTED IMIDAZOLES

(75) Inventors: Wilfried Schwab, Werder (DE); Guido Schiffer, Wuppertal (DE); Kurt Voegtli, Oberhofen (CH); Andreas Kyas, Wehr (DE); Gerd Osswald, Aarau Rohr (CH)

(73) Assignee: AICURIS GMBH & CO. KG, Wuppertal (DE)

( * ) Notice: Subject to any disclaimer, the term of this patent is extended or adjusted under 35 U.S.C. 154(b) by 0 days.

(21) Appl. No.: 14/344,995

(22) PCT Filed: Sep. 12, 2012

(86) PCT No.: PCT/EP2012/067814
§ 371 (c)(1),
(2), (4) Date: May 16, 2014

(87) PCT Pub. No.: WO2013/037812
PCT Pub. Date: Mar. 21, 2013

(65) Prior Publication Data
US 2014/0315924 A1    Oct. 23, 2014

(30) Foreign Application Priority Data
Sep. 14, 2011 (DE) .......................... 10 2011 113 749

(51) Int. Cl.
*A61K 31/496* (2006.01)
*C07D 401/12* (2006.01)
*C07C 309/04* (2006.01)

(52) U.S. Cl.
CPC ............ *C07D 401/12* (2013.01); *A61K 31/496* (2013.01); *C07C 309/04* (2013.01)

(58) Field of Classification Search
None
See application file for complete search history.

(56) References Cited

U.S. PATENT DOCUMENTS

| 3,609,152 | A | * | 9/1971 | Hess et al. ..................... 540/600 |
| 4,337,341 | A | * | 6/1982 | Zimmerman .................. 546/112 |
| 7,820,657 | B2 | * | 10/2010 | Bhagwat et al. ........... 514/233.2 |
| 7,919,489 | B2 |  | 4/2011 | Zimmermann et al. |
| 2008/0176859 | A1 |  | 7/2008 | Zimmermann et al. |
| 2010/0166673 | A1 | * | 7/2010 | Surber et al. .................... 424/45 |

FOREIGN PATENT DOCUMENTS

WO    2006089664 A2    8/2006

OTHER PUBLICATIONS

Elder et al. J.Pharm. Sciences, vol. 99, pp. 2948-2961 (2010).*
Vippagunta et al. Advanced Drig Delivery Reviews, vol. 48, pp. 3-26 (2001).*
Drug Evaluations by American Medical Association (6th Ed.), pp. 1615-1616 (1986).*
International Search Report for PCT/EP2012/067814 dated Nov. 11, 2012.
Berge, S. M. et al., "Pharmaceutical Satls," Journal of Pharmaceutical Sciences, Jan. 1977, vol. 66, No. 1, pp. 1-19.
Heinrich, P. et al., "Handbook of Pharmaceutical Salts: Properties, Selection, and Use," International Union of Pure and Applied Chemistry (IUPAC), pp. 212-217.

* cited by examiner

*Primary Examiner* — Emily Bernhardt
(74) *Attorney, Agent, or Firm* — Millen, White, Zelano & Branigan, P.C.

(57) ABSTRACT

The invention relates to sulfonic acid salts of heterocyclylamide-substituted imidazoles, and to solvates and hydrates thereof, to the use thereof for treating and/or preventing diseases, and to use thereof for producing drugs for treating and/or preventing diseases, in particular for use as antiviral agents, in particular against cytomegaloviruses.

20 Claims, 1 Drawing Sheet

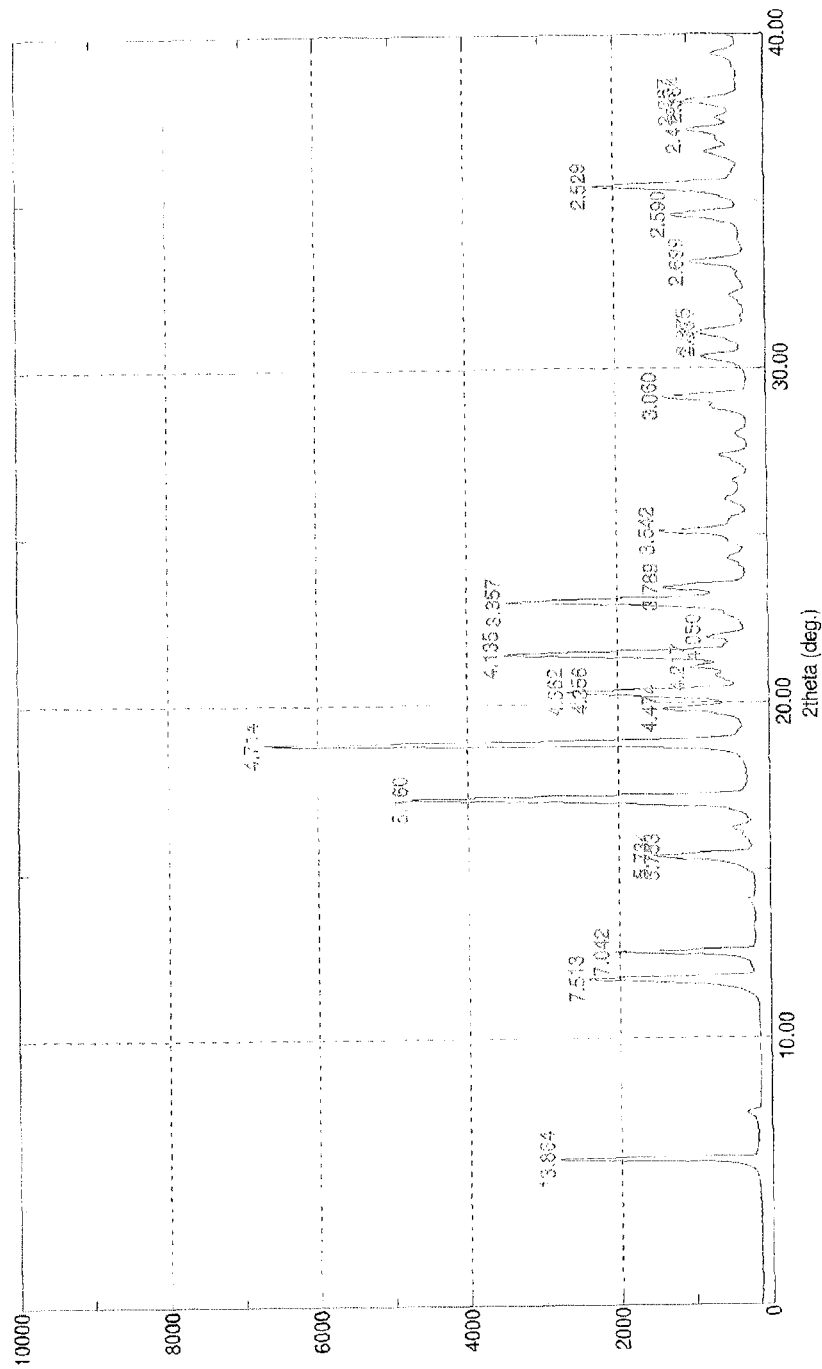

SULFONIC ACID SALTS OF HETEROCYCLYLAMIDE-SUBSTITUTED IMIDAZOLES

This invention relates to salts of the compounds of the formula

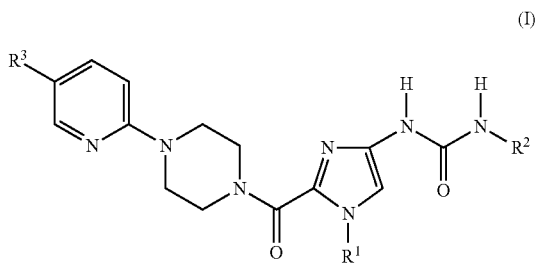

in which
R$^1$ stands for methyl, ethyl, butyl, or cyclopropylmethyl,
R$^2$ stands for phenyl, whereby phenyl is substituted with a substituent that is selected from the group that consists of trifluoromethoxy and difluoromethoxy, and
R$^3$ stands for hydrogen, methyl, chlorine, methoxy, or trifluoromethyl.

The invention further relates to a method for their production, their use for the treatment and/or prevention of diseases, as well as their use for the production of pharmaceutical agents for the treatment and/or prevention of diseases, in particular for use as antiviral agents, in particular against cytomegaloviruses.

The compounds of Formula (I) are known from, e.g., WO 2006/089664 and were developed by the applicant as promising candidates for antivirally effective substances, in particular for combating infections with the human cytomegalovirus (HCMV). In development, it has been shown, however, that the substances in aqueous solvents as well as strongly polar solvents showed an inadequate solubility. The problems with respect to the solubility were still further intensified in that the compounds also showed inadequate solubility under the conditions existing in the human stomach (approximately 0.1 M HCl, pH~1), in which the process can be started from the in-situ formation of an HCl salt.

It is thus an object of the invention to describe salts that show a considerably improved solubility in comparison to the free base of the compounds of Formula (I). Further, these salts should also be stable over the long term under the usual storage conditions. In particular, the compounds should not show any elevated hygroscopy. Also, the salts in the presence of a dilute HCL solution should be converted only slowly into the HCl salt in order to ensure as quick and uniform a release as possible even under conditions as are present in the human stomach.

Surprisingly enough, it was discovered that the organic sulfonic acid salts of the compounds of Formula (I) show a superior solubility in comparison to the free base, as well as a broad spectrum of other salts of the compounds of Formula (I). Further, these salts also show the long-term stability that is necessary for use in medications. In addition, it has been shown that the salts according to the invention also show a high and uniform solubility under conditions that correspond to those in the human stomach.

Subjects of the invention are salts of the compounds of Formula (I) with an organic sulfonic acid or solvates or hydrates thereof.

Within the scope of the invention, salts of organic sulfonic acids are adducts of a reaction of a compound of Formula (I) with an organic sulfonic acid. In this connection, the compounds of Formula (I) and the organic sulfonic acids can be present in any ratio. In this case, the ratio is preferably in whole numbers (e.g., 1:1, 1:2, 1:3, 3:1, 2:1). In this case, these salts can be produced by a direct reaction of the compounds of Formula (I) with an organic sulfonic acid or by the production of other acid salts of the compounds of Formula (I) followed by an exchange of the counterion.

Within the scope of the invention, those forms of the compounds according to the invention that form a complex by coordination with solvent molecules are referred to as solvates. Hydrates are a special form of solvates, in which the coordination with water is carried out.

Within the scope of this invention, the salts in which the organic sulfonic acid is methanesulfonic acid are preferred.

Within the scope of the invention, the dimesylate salts are especially preferred.

Within the scope of the invention, a salt with the following formula is preferred:

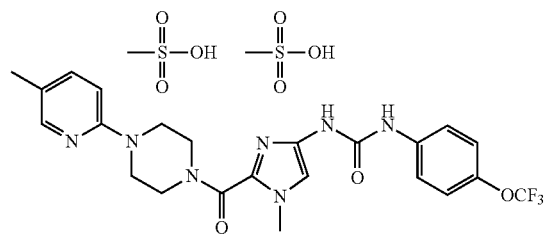

Within the scope of the invention, in particular a crystalline N-(1-methyl-2-{[4-(5-methylpyridin-2-yl)piperazin-1-yl]-carbonyl}-1H-imidazol-4-yl)-N'-[4-trifluoromethoxyphenyl]urea dimesylate, which shows characteristic peaks at approximately 6.37, 11.77, 12.56, 17.17, 18.81, 20.34, 21.47, 23.04, 35.46 degrees 2-theta in the powder-XRD diffractogram, is preferred.

Within the scope of the invention, crystalline N-(1-methyl-2-{[4-(5-methylpyridin-2-yl)piperazin-1-yl]-carbonyl}-1H-imidazol-4-yl)-N'-[4-trifluoromethoxyphenyl]urea dimesylate, which shows a powder-XRD diffractogram, as essentially depicted in FIG. 1, is further preferred.

The salts according to the invention are in general produced by reaction of a compound of Formula (I) with an organic sulfonic acid in a solvent.

It is further possible to produce the salts according to the invention by reaction of an acid salt of the compounds of Formula (I), which is not a salt of an organic sulfonic acid, with a source for sulfonate anions of an organic sulfonic acid in a solvent.

In the latter case, the source for sulfonate anions can be an organic sulfonic acid or a salt of an organic sulfonic acid.

A subject of the invention is thus further a method for the production of organic sulfonic acid salts of the compounds of Formula (I), which comprises the reaction of compounds of Formula (I) or salts of the compounds of Formula (I), which are not acid salts of an organic sulfonic acid, with an organic sulfonic acid or a source of organic sulfonate anions in a solvent.

The solvent is preferably selected in such a way that it offers a good balance between the solubility of the compounds of Formula (I) or the salts of the compound of Formula (I), which are not sulfonic acid salts, and the organic sulfonic acid or the source of sulfonate anions. Preferably, the salts according to the invention in the solvent that is used should be as sparingly soluble as possible. Optionally, the salts according to the invention can, however, also be precipitated out by adding a counter solvent.

Examples of solvents that are used for the production of the salts according to the invention include the following: namely alcohols, such as methanol, ethanol, n-propanol, isopropanol, and butanol; ethers, such as diethyl ether, methyl-tert-butyl ether, 1,2-dimethoxyethane, dioxane or tetrahydrofuran; hydrocarbons, such as benzene or toluene; or other solvents, such as acetone, ethyl acetate, methyl ethyl ketone, methyl isobutyl ketone, acetonitrile, heptane, dimethyl sulfoxide or dimethylformamide.

Optionally, for precipitating out the salts according to the invention, a counter solvent is added. Examples of such counter solvents include the following: namely water and alcohols, such as methanol, ethanol, or propanol.

The salts that are thus obtained according to the invention can optionally be further processed, e.g., recrystallized or micronized, in order to further adapt their physical properties to the application.

The heterocyclylamide-substituted imidazoles used for the production of the salts according to the invention are known and can be produced, e.g., according to the method that is described in WO 2006/089664.

In particular, the production of the heterocyclylamide-substituted imidazoles that are used is carried out by the reaction of compounds of the formula

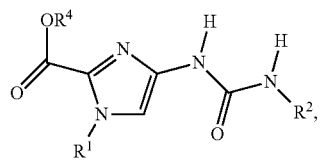

(II)

in which
$R^1$ and $R^2$ are as defined above, and
$R^4$ stands for methyl or ethyl,
in the first stage with a base and in the second stage with compounds of the formula

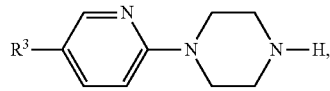

(III)

in which
$R^3$ is as defined above,
in the presence of dehydrating reagents.

The reaction in the first stage is carried out in general in inert solvents, preferably in a temperature range of 0° C. until reflux of the solvent occurs at normal pressure.

Bases are, for example, alkali hydroxides such as sodium hydroxide, lithium hydroxide, or potassium hydroxide, or alkali carbonates such as cesium carbonate, sodium carbonate or potassium carbonate. In this case, sodium hydroxide is preferred.

Inert solvents are, for example, halogenated hydrocarbons, such as methylene chloride, trichloromethane, tetrachloromethane, trichloroethane, tetrachloroethane, 1,2-dichloroethane or trichloroethylene; ethers, such as diethyl ether, methyl-tert-butyl ether, 1,2-dimethoxyethane, dioxane, tetrahydrofuran, glycol dimethyl ether, or diethylene glycol dimethyl ether; alcohols, such as methanol, ethanol, n-propanol, iso-propanol, n-butanol or tert-butanol; hydrocarbons, such as benzene, xylene, toluene, hexane, cyclohexane or crude oil fractions; or other solvents, such as dimethylformamide, dimethylacetamide, dimethyl sulfoxide, acetonitrile or pyridine, or mixtures of solvents with water. As a solvent, a mixture of ethanol and water is preferred.

The reaction in the second stage is carried out in general in inert solvents, optionally in the presence of a base, preferably in a temperature range of −70° C. to 40° C. at normal pressure.

As dehydrating reagents, in this connection, for example, carbodiimides, such as, e.g., N,N'-diethyl-, N,N'-dipropyl-, N,N'-diisopropyl-, N,N'-dicyclohexyl-carbodiimide, N-(3-dimethylaminoisopropyl)-N'-ethylcarbodiimide-hydrochloride (EDC), N-cyclohexylcarbodiimide-N'-propyloxymethyl-polystyrene (PS-carbodiimide); or carbonyl compounds, such as carbonyl diimidazole; or 1,2-oxazolium compounds, such as 2-ethyl-5-phenyl-1,2-oxazolium-3-sulfate or 2-tert-butyl-5-methyl-isoxazolium-perchlorate; or acylamino compounds, such as 2-ethoxy-1-ethoxycarbonyl-1,2-dihydroquinoline, or propanephosphonic acid anhydride, or isobutyl chloroformate, or bis-(2-oxo-3-oxazolidinyl) phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxy-benzotriazole (HOBt) or benzotriazol-1-yloxytris(dimethylamino)phosphonium hexafluorophosphate (BOP) or mixtures of the latter, with bases, are suitable.

Bases are, for example, alkali carbonates, such as, e.g., sodium carbonate or potassium carbonate or potassium bicarbonate; or organic bases, such as trialkylamines, e.g., triethylamine, N-methylmorpholine, N-methylpiperidine, 4-dimethylaminopyridine, or diisopropylethylamine or DBU, DBN, or pyridine; N-methylmorpholine is preferred.

The condensation with propanephosphonic acid anhydride (T3P) is preferably performed in the presence of N-methylmorpholine (NMM).

Inert solvents are, for example, halogenated hydrocarbons, such as methylene chloride, trichloromethane, tetrachloromethane, trichloroethane, tetrachloroethane, 1,2-dichloroethane, or trichloroethylene; ethers, such as diethyl ether, methyl-tert-butyl ether, 1,2-dimethoxyethane, dioxane, tetrahydrofuran, glycol dimethyl ether, or diethylene glycol dimethyl ether; hydrocarbons, such as benzene, xylene, toluene, hexane, cyclohexane or crude oil fractions; or other solvents, such as ethyl acetate, acetone, dimethylformamide, dimethylacetamide, 2-butanone, dimethyl sulfoxide, acetonitrile or pyridine, in the case of water-miscible solvents also mixtures of the same with water; dimethylformamide is preferred.

The compounds of Formula (II) are known or can be produced by compounds of Formula (IV)

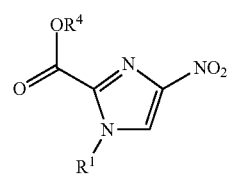

(IV)

in which
$R^1$ and $R^4$ are as defined above,
being reacted in the first stage with a reducing agent and in the second stage in the presence of a carbonic acid derivative with compounds of the formula $$H_2N-R^2 \qquad\qquad (V)$$

in which
R² is as defined above,
or being reacted in the second stage with compounds of the formula $$OCN\text{—}R^2, \quad (VI)$$

in which
R² is as defined above.

In this case, the reaction is carried out in the first stage in general in inert solvents, preferably in a temperature range of 0° C. until reflux of the solvent occurs at normal pressure up to 3 bar.

Reducing agents are, for example, palladium on activated carbon and hydrogen, formic acid/triethylamine/palladium on activated carbon, zinc, zinc/hydrochloric acid, iron, iron/hydrochloric acid, iron(II) sulfate/hydrochloric acid, sodium sulfide, sodium disulfide, sodium dithionite, ammonium polysulfide, sodium borohydride/nickel chloride, tin dichloride, titanium trichloride or Raney nickel and aqueous hydrazine solution; Raney nickel and aqueous hydrazine solution, palladium on activated carbon and hydrogen or formic acid/triethylamine/palladium on activated carbon are preferred.

Inert solvents are, for example, ethers, such as diethyl ether, methyl-tert-butyl ether, 1,2-dimethoxyethane, dioxane, tetrahydrofuran, glycol dimethyl ether, or diethylene glycol dimethyl ether; alcohols, such as methanol, ethanol, n-propanol, isopropanol, n-butanol, or tert-butanol; hydrocarbons, such as benzene, xylene, toluene, hexane, cyclohexane or crude oil fractions; or other solvents, such as dimethylformamide, dimethylacetamide, acetonitrile or pyridine, in the case of water-miscible solvents also mixtures of the same with water. As solvents, methanol, ethanol, isopropanol are preferred, or in the case of Raney nickel and aqueous hydrazine solution, tetrahydrofuran is preferred.

The reaction in the second stage according to the first variant is carried out in general in inert solvents, preferably in a temperature range from room temperature up to 40° C. at normal pressure.

Carbonic acid derivatives are, for example, N,N-carbonyldiimidazole, phosgene, diphosgene, triphosgene, phenyl chloroformate, or chloroformic acid-4-nitrophenylester; N,N-carbonyldiimidazole is preferred.

Inert solvents are, for example, halogenated hydrocarbons, such as methylene chloride, trichloromethane, tetrachloromethane, trichloroethane, tetrachloroethane, 1,2-dichloroethane, or trichloroethylene; ethers, such as diethyl ether, methyl-tert-butyl ether, 1,2-dimethoxyethane, dioxane, tetrahydrofuran, glycol dimethyl ether or diethylene glycol dimethyl ether; hydrocarbons, such as benzene, xylene, toluene, hexane, cyclohexane or crude oil fractions; or other solvents, such as ethyl acetate, acetone, dimethylformamide, dimethylacetamide, 2-butanone, dimethyl sulfoxide, acetonitrile or pyridine, and in the case of water-miscible solvents also mixtures of the same with water; dimethyl sulfoxide is preferred.

The reaction in the second stage according to the second variant is carried out in general in inert solvents, optionally in the presence of a base, preferably in a temperature range from room temperature until reflux of the solvent occurs at normal pressure.

Inert solvents are, for example, halogenated hydrocarbons, such as methylene chloride, trichloromethane, tetrachloromethane, trichloroethane, tetrachloroethane, 1,2-dichloroethane or trichloroethylene; ethers, such as diethyl ether, methyl-tert-butyl ether, 1,2-dimethoxyethane, dioxane, tetrahydrofuran, glycol dimethyl ether or diethylene glycol dimethyl ether; hydrocarbons, such as benzene, xylene, toluene, hexane, cyclohexane or crude oil fractions; or other solvents, such as ethyl acetate, acetone, dimethylformamide, dimethylacetamide, 2-butanone, dimethyl sulfoxide, acetonitrile or pyridine; tetrahydrofuran or methylene chloride is preferred.

Bases are, for example, alkali carbonates such as cesium carbonate, sodium carbonate, or potassium carbonate, or potassium-tert-butanolate, or other bases such as sodium hydride, DBU, triethylamine, or diisopropylethylamine, preferably triethylamine.

The compounds of Formula (IV) are known or can be produced by compounds of the formula

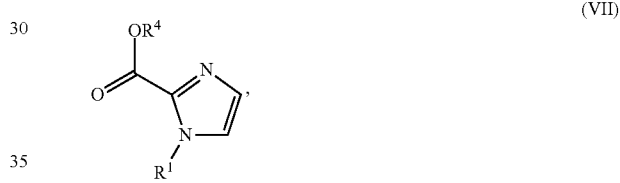

in which
R¹ and R⁴ are as defined above,
being reacted with fuming nitric acid, concentrated nitric acid, nitrating acid, or other mixing ratios of sulfuric and nitric acid, optionally in acetic anhydride as solvent, preferably in a temperature range from room temperature up to 60° C. at normal pressure.

The compounds of Formulas (III), (IV), (V), (VII) are known or can be synthesized from the corresponding educts according to known methods.

The production of the heterocyclylamide-substituted imidazoles used for the production of the salts according to the invention is explained in more detail by way of example in the synthesis diagram below. In this connection, the synthesis diagram is defined purely by way of example and is in no way limiting.

Synthesis Diagram:

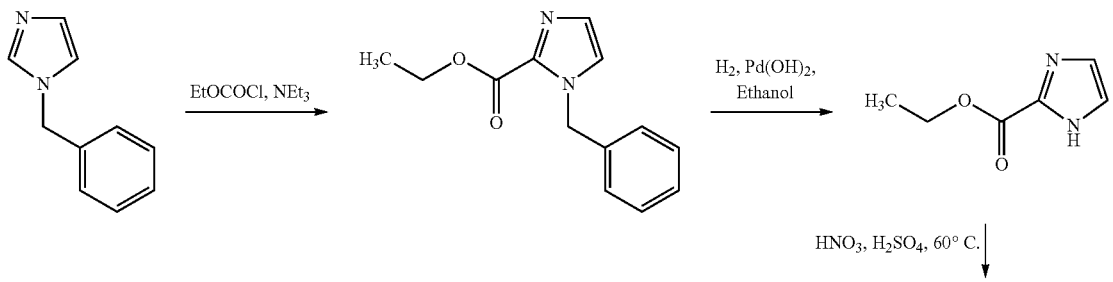

-continued

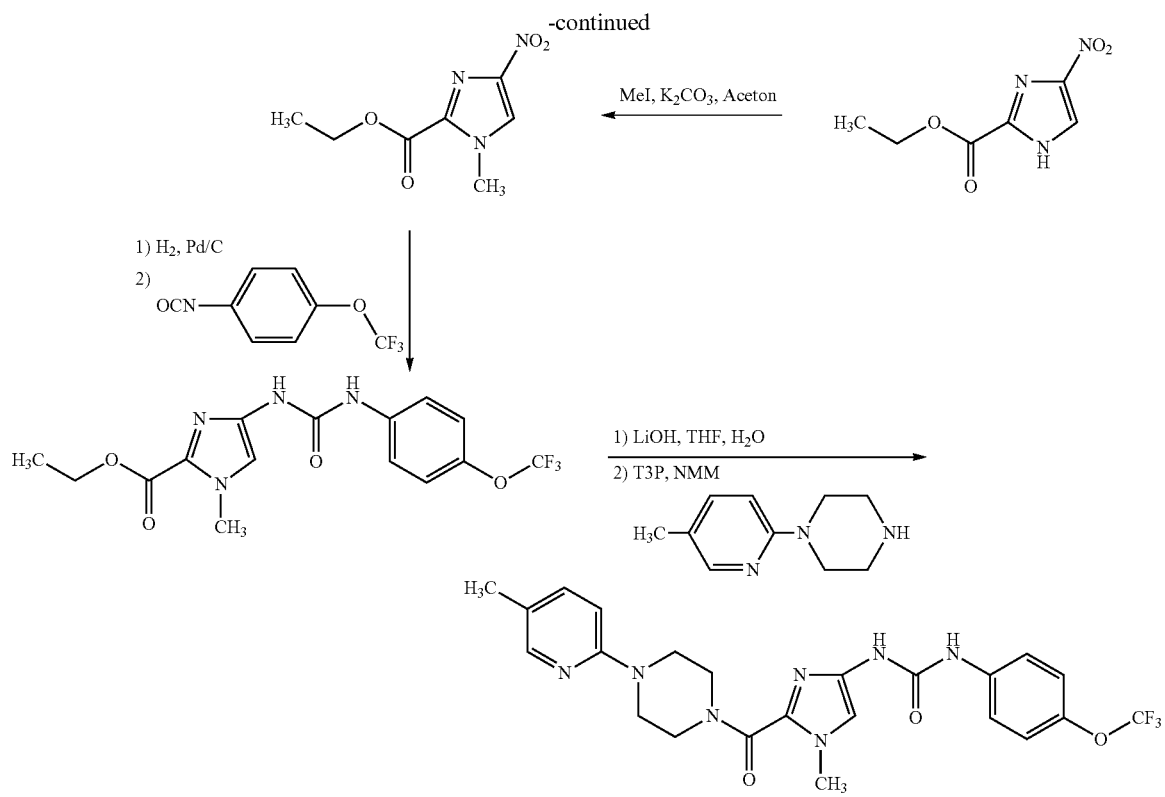

[Key:]
Aceton = Acetone

The salts according to the invention show an antiviral action relative to representatives of the group Herpesviridae (Herpes viruses), primarily relative to cytomegaloviruses (CMV), in particular relative to the human cytomegalovirus (HCMV). They are thus suitable for the treatment and/or prevention of diseases, primarily infections with viruses, in particular the viruses mentioned herein, and the infectious diseases that are produced as a result. Herein, a viral infection is defined both as an infection with a virus as well as a disease caused by an infection with a virus.

The salts according to the invention can be used based on their special properties for the production of pharmaceutical agents that are suitable for the prevention and/or treatment of diseases, in particular viral infections.

As types of indications, the following can be mentioned:
1) Treatment and prevention of HCMV infections in AIDS patients (retinitis, pneumonitis, gastrointestinal infections).
2) Treatment and prevention of cytomegaloviral infections in bone marrow and organ transplant patients, who often come down with life-threatening versions of an HCMV pneumonitis, HCMV encephalitis, as well as gastrointestinal and systemic HCMV infections.
3) Treatment and prevention of HCMV infections in newborns and toddlers.
4) Treatment of an acute HCMV infection in pregnant women.
5) Treatment of the HCMV infection in immunosuppressed patients with cancer and cancer therapy.
Treatment of HCMV-positive cancer patients with the purpose of reducing the progression of HCMV-mediated tumors (cf. J. Cinatl, et al., *FEMS Microbiology Reviews* 2004, 28, 59-77).

The salts according to the invention for the production of pharmaceutical agents are preferably used that are suitable for the prevention and/or treatment of infections with a representative of the group Herpesviridae, especially a cytomegalovirus, in particular the human cytomegalovirus.

Based on their pharmacological properties alone and if necessary also in combination with other active ingredients, in particular antiviral active ingredients such as, for example, valganciclovir, ganciclovir, valacyclovir, acyclovir, foscarnet, cidofovir and related derivatives, the salts according to the invention can be used for the treatment and/or prevention of viral infections, in particular HCMV infections.

Another subject of this invention is the use of the salts according to the invention in a method for the treatment and/or prevention of diseases, preferably viral infections, in particular infections with the human cytomegalovirus (HCMV) or another representative of the group Herpesviridae.

Another subject of this invention is the use of salts according to the invention for the treatment and/or prevention of diseases, in particular the above-mentioned diseases.

Another subject of this invention is the use of the salts according to the invention for the production of a pharmaceutical agent for the treatment and/or prevention of diseases, in particular the above-mentioned diseases.

Another subject of this invention is a method for the treatment and/or prevention of diseases, in particular the above-mentioned diseases, with use of an antivirally effective amount of the salts according to the invention.

The salts according to the invention can have a systemic and/or local effect. For this purpose, they can be administered in a suitable way, such as by the following means, e.g., oral, parenteral, pulmonary, nasal, sublingual, lingual, buccal, rectal, dermal, transdermal, conjunctival, otic, or as an implant or stent.

For these administration methods, the salts according to the invention can be administered in suitable forms of administration.

For oral administration, the forms of administration that deliver salts according to the invention in a quick-acting and/or modified manner and that contain the compounds according to the invention in crystalline and/or amorphized and/or dissolved form, such as, e.g., tablets (uncoated or coated tablets, for example with gastric juice-resistant or slow-dissolving or insoluble coatings, which control the release of the compound according to the invention), tablets or films/wafers that quickly dissolve in the oral cavity, films/lyophilisates, capsules (for example, hard or soft gelatin capsules), coated tablets, granulates, pellets, powders, emulsions, suspensions, aerosols or solutions, are suitable according to the state of the art.

Parenteral administration can be done by bypassing a resorption step (e.g., by intravenous, intraarterial, intracardial, intraspinal or intralumbar means) or by including resorption (e.g., by intramuscular, subcutaneous, intracutaneous, percutaneous or intraperitoneal means). For the parenteral administration, i.a., injection and infusion preparations in the form of solutions, suspensions, emulsions, lyophilisates, or sterile powders are suitable as forms of administration.

For the other administration methods, e.g., inhalation forms of medication (i.a., powder inhalers, nebulizers), nose drops, nasal solutions, nasal sprays; tablets that are to be administered lingually, sublingually or buccally; films/wafers or capsules, suppositories, ear or eye preparations, vaginal capsules, aqueous suspensions (lotions, shaking mixtures), lipophilic suspensions, ointments, creams, transdermal therapeutic systems, milk, pastes, foams, scattered powders, implants or stents are suitable.

The salts according to the invention can be converted into the cited forms of administration. This can take place in a way that is known in the art by mixing with inert, nontoxic, pharmaceutically suitable adjuvants. These adjuvants include, i.a., vehicles (for example, microcrystalline cellulose, lactose, mannitol), solvents (e.g., liquid polyethylene glycols), emulsifiers and dispersing agents or wetting agents (for example, sodium dodecyl sulfate, polyoxysorbitanoleate), binders (for example, polyvinylpyrrolidone), synthetic and natural polymers (for example, albumin), stabilizers (e.g., antioxidants such as, for example, ascorbic acid), dyes (e.g., inorganic pigments, such as, for example, iron oxides), and flavoring and/or odor correctives.

Within the scope of the invention, a pharmaceutical agent that has 5 to 12.5 mg/ml of a salt according to the invention, 50 to 150 mg/ml of hydroxypropyl-β-cyclodextrin, 0.5 to 2.0 mg/ml of sodium acetate as well as water, and optionally other pharmaceutically harmless adjuvants is preferred.

Other subjects of this invention are pharmaceutical agents that contain at least one salt according to the invention, usually together with one or more inert, non-toxic, pharmaceutically suitable adjuvants, as well as their use for the above-mentioned purposes.

In general, it has proven advantageous, in the case of intravenous administration, to administer amounts, relative to the pure active ingredient, of approximately 0.001 to 10 mg/kg, preferably approximately 0.01 to 5 mg/kg, of body weight, to achieve effective results. In the case of oral administration, the metering is usually approximately 0.01 to 25 mg/kg, preferably 0.1 to 10 mg/kg, of body weight.

Nevertheless, it may optionally be necessary to deviate from the above-mentioned amounts, specifically based on body weight, administration method, individual behavior relative to the active ingredient, type of preparation and time or interval at which the administration is done. Thus, in some cases, it may be sufficient to get by with less than the above-mentioned minimum amount, while in other cases, the above-mentioned upper limit must be exceeded. In the case of the administration of larger amounts, it may be advisable to distribute the latter in several individual administrations over the day.

BRIEF DESCRIPTION OF DRAWINGS

The invention is now explained in more detail below based on the examples as well as in reference to the accompanying drawing. Here:

FIG. 1: shows a powder-XRD diffractogram of the salt of Example 1.

The percentages in the following tests and examples are, if not otherwise indicated, percents by weight; parts are parts by weight. Solvent ratios, dilution ratios, and concentration information of liquid/liquid solutions in each case relate to the volume.

EXAMPLES

Abbreviations that are Used

Ex. Example
TLC Thin-Layer Chromatography
DMF N,N-Dimethylformamide
DMSO Dimethyl Sulfoxide
d. Th. of Theory
EI Electron Impact Ionization (in MS)
ESI Electrospray Ionization (in MS)
h Hour
HPLC High-Pressure-, High-Performance Liquid Chromatography
LC-MS Liquid Chromatography-Coupled Mass Spectroscopy
MS Mass Spectroscopy
NMR Nuclear Resonance Spectroscopy
RP-HPLC Reverse-Phase HPLC
RT Room Temperature
$R_t$ Retention Time (with HPLC)
TBTU O-(Benzotriazol-1-yl)-N,N,N',N'-tetramethyluronium tetrafluoroborate
THF Tetrahydrofuran
HPLC- and LC-MS Methods:
Method 1 (LC-MS):
  Instrument: Micromass Quattro LCZ with HPLC Agilent Series 1100; Column: Phenomenex Synergi 2μ Hydro-RP Mercury 20 mm×4 mm; Eluant A: 1 l of water+0.5 ml of 50% formic acid, Eluant B: 1 l of acetonitrile+0.5 ml of 50% formic acid; Gradient: 0.0 min 90% A 2.5 min 30% A 3.0 min 5% A 4.5 min 5% A; Flow: 0.0 min 1 ml/min, 2.5 min/3.0 min/4.5 min 2 ml/min; Oven: 50° C.; UV detection: 208-400 nm.
Method 2 (LC-MS):
  Instrument: Micromass Platform LCZ with HPLC Agilent Series 1100; Column: Phenomenex Synergi 2μ Hydro-RP Mercury 20 mm×4 mm; Eluant A: 1 l of water+0.5 ml of 50% formic acid, Eluant B: 1 l of acetonitrile+0.5 ml of 50% formic acid; Gradient: 0.0 min 90% A 2.5 min 30% A 3.0 min 5% A 4.5 min 5% A; Flow: 0.0 min 1 ml/min, 2.5 min/3.0 min/4.5 min 2 ml/min; Oven: 50° C.; UV detection: 210 nm.

Method 3 (LC-MS):

Device type MS: Micromass ZQ; Device type HPLC: Waters Alliance 2795; Column: Phenomenex Synergi 2μ Hydro-RP Mercury 20 mm×4 mm; Eluant A: 1 l of water+0.5 ml of 50% formic acid, Eluant B: 1 l of acetonitrile+0.5 ml of 50% formic acid; Gradient: 0.0 min 90% A 2.5 min 30% A 3.0 min 5% A 4.5 min 5% A; Flow: 0.0 min 1 ml/min, 2.5 min/3.0 min/4.5 min 2 ml/min; Oven: 50° C.; UV detection: 210 nm.

Method 4 (LC-MS):

Device type MS: Micromass ZQ; Device type HPLC: HP 1100 Series; UV DAD; Column: Phenomenex Synergi 2μ Hydro-RP Mercury 20 mm×4 mm; Eluant A: 1 l of water+0.5 ml of 50% formic acid, Eluant B: 1 l of acetonitrile+0.5 ml of 50% formic acid; Gradient: 0.0 min 90% A 2.5 min 30% A 3.0 min 5% A 4.5 min 5% A; Flow: 0.0 min 1 ml/min, 2.5 min/3.0 min/4.5 min 2 ml/min; Oven: 50° C.; UV detection: 210 nm.

Method 5 (Analytical HPLC):

Column: Kromasil 100 RP-18, 60 mm×2.1 mm, 3.5 μm; Eluant A: water+0.5% perchloric acid (70%), Eluant B: acetonitrile; Gradient: 0 min 2% B, 0.5 min 2% B, 4.5 min 90% B, 9 min 90% B, 9.2 min 2% B, 10 min 2% B; Flow: 0.75 ml/min; Column temperature: 30° C.; Detection: UV 210 nm.

Starting Compounds

Example 1A 1-(Cyclopropylmethyl)-4-[({[4-(trifluoromethoxy)phenyl]amino}carbonyl)amino]-1H-imidazole-2-carboxylic acid

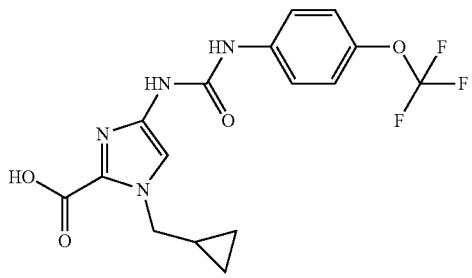 [SMILES: O=C(Nc1ccc(OC(F)(F)F)cc1)Nc1cn(CC2CC2)c(C(=O)O)n1]

Stage 1

1-(Cyclopropylmethyl)-4-nitro-1H-imidazole-2-carboxylic acid ethyl ester

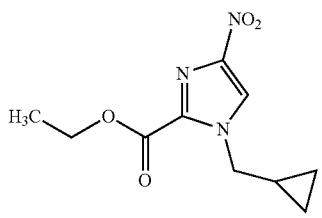 [SMILES: CCOC(=O)c1nc([N+](=O)[O-])cn1CC1CC1]

15 g (81 mmol) of 4-nitro-1H-imidazole-2-carboxylic acid ethyl ester is stirred under argon together with 13.13 g (97.2 mmol) of cyclopropyl methyl bromide and 22.4 g (162 mmol) of potassium carbonate in 165 ml of DMF for 1 hour at 80° C. After cooling, the reaction mixture is diluted with water and extracted four times with ethyl acetate. The combined organic phases are washed once with water and three times with saturated sodium chloride solution, dried with magnesium sulfate, and concentrated by evaporation in a vacuum. The crystalline residue is immediately reused for the next reaction.

Yield: 17.59 g (70% of theory)
LC-MS (Method 1): $R_t$=2.02 min.
MS (ESI$^+$): m/z=240 [M+H]$^+$
$^1$H-NMR (300 MHz, DMSO-$d_6$): δ=8.2 (s, 1H), 4.4 (q, 2H), 4.3 (d, 2H), 1.4 (m, 4H), 0.55 (q, 2H), 0.45 (q, 2H) ppm.

Stage 2

4-Amino-1-(cyclopropylmethyl)-1H-imidazole-2-carboxylic acid ethyl ester

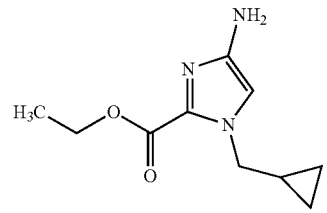

3.89 g (16.26 mmol) of 1-(cyclopropylmethyl)-4-nitro-1H-imidazole-2-carboxylic acid ethyl ester is dissolved in 50 ml of THF and mixed with a spatula tip full of Raney nickel. The reaction mixture is hydrogenated with hydrogen in a hydrogenating apparatus at room temperature. The catalyst is filtered off, and the filtrate is concentrated by evaporation in a vacuum. The evaporation residue is reused immediately for the next reaction.

Yield: 3.46 g (100% of theory)
LC-MS (Method 2): $R_t$=1.21 min.
MS (ESI$^+$): m/z=210 [M+H]$^+$
$^1$H-NMR (300 MHz, DMSO-$d_6$): δ=6.55 (s, 1H), 4.55 (s, 2H), 4.2 (q, 2H), 4.1 (d, 2H), 1.25 (tr, 3H), 1.2 (m, 1H), 0.5 (q, 2H), 0.3 (q, 2H) ppm.

Stage 3

4-[({[4-(Trifluoromethoxy)phenyl]amino}carbonyl)amino]-1-(cyclopropylmethyl)-1H-imidazole-2-carboxylic acid ethyl ester

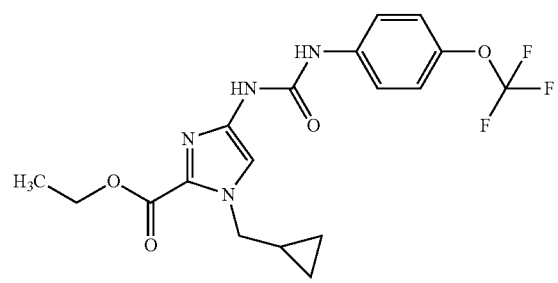 [SMILES: CCOC(=O)c1nc(NC(=O)Nc2ccc(OC(F)(F)F)cc2)cn1CC1CC1]

7.49 g (35.8 mmol) of 4-amino-1-(cyclopropylmethyl)-1H-imidazole-2-carboxylic acid ethyl ester is mixed in 18 ml of THF under argon with 6 g (35.8 mmol) of 4-(trifluoromethoxy)phenylisocyanate and stirred for 4 hours at room temperature. The reaction mixture is concentrated by evaporation in a vacuum, and the product that crystallizes out in this case is stirred in 40 ml of ethyl acetate and suctioned off.

Yield: 11.1 g (82% of theory)
LC-MS (Method 1): $R_t$=2.66 min.
MS (ESI+): m/z=376 [M+H]+
$^1$H-NMR (300 MHz, DMSO-$d_6$): δ=9.45 (s, 1H), 8.0 (d, 1H), 7.35 (s, 1H), 7.3 (d, 1H), 7.2 (dd, 1H), 4.3 (q, 2H), 4.25 (d, 2H), 2.25 (s, 3H), 1.3 (tr, 3H), 1.25 (m, 1H), 0.55 (q, 2H), 0.35 (q, 2H) ppm.

Stage 4

4-[({[4-(Trifluoromethoxy)phenyl]amino}carbonyl)amino]-1-(cyclopropylmethyl)-1H-imidazole-2-carboxylic acid

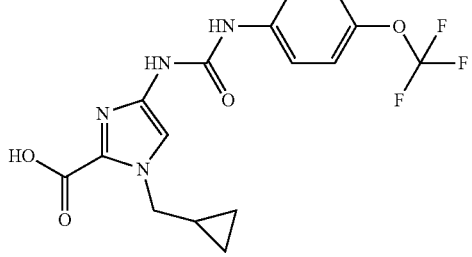

10.6 g (28.1 mmol) of 4-[({[4-(trifluoromethoxy)phenyl]amino}-carbonyl)amino]-1-(cyclopropylmethyl)-1H-imidazole-2-carboxylic acid ethyl ester is suspended in 158 ml of ethanol. While being cooled with ice, 16.4 ml of water and 6 ml (112 mmol) of 50% aqueous sodium hydroxide solution are added. The reaction mixture is stirred for 1 hour at room temperature and then concentrated by evaporation in a vacuum. The residue is taken up in 100 ml of isopropanol and mixed with 100 ml of 1N hydrochloric acid while being cooled with ice. The crystals are suctioned off and dried in a vacuum at 40° C.

Yield: 9.85 g (100% of theory)
LC-MS (Method 3): $R_t$=1.74 min.
MS (ESI+): m/z=349 [M+H]+
$^1$H-NMR (400 MHz, DMSO-$d_6$): δ=9.4 (s, 1H), 8.0 (d, 1H), 7.3 (s, 1H), 7.25 (d, 1H), 7.2 (dd, 1H), 4.25 (d, 2H), 2.25 (s, 3H), 1.25 (m, 1H), 0.55 (q, 2H), 0.35 (q, 2H) ppm.

Example 2A

1-Butyl-4-[({[4-(trifluoromethoxy)phenyl]amino}carbonyl)amino]-1H-imidazole-2-carboxylic acid

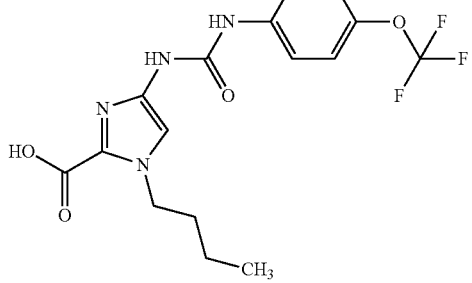

Production is done analogously to Example 1A.
Yield: 2.05 g (96% of theory)
LC-MS (Method 3): $R_t$=1.96 min.
MS (ESI+): m/z=387 [M+H]+

$^1$H-NMR (300 MHz, DMSO-$d_6$): δ=9.0 (s, 1H), 8.9 (s, 1H), 7.55 (d, 2H), 7.3 (s, 1H), 7.25 (d, 1H), 4.35 (tr, 2H), 1.7 (quintet, 2H), 1.25 (sextet, 2H), 0.9 (tr, 3H) ppm.

Example 3A

1-Methyl-4-[({[4-(trifluoromethoxy)phenyl]amino}carbonyl)amino]-1H-imidazole-2-carboxylic acid ethyl ester

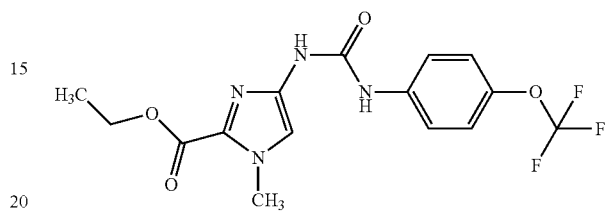

1.22 g (3.61 mmol) of 4-amino-1-methyl-1H-imidazole-2-carboxylic acid ethyl ester (synthesis analogous to Example 1A, Stage 3, or else according to Tetrahedron Lett. 2003, 44, 1607 and literature cited there) is mixed in 50 ml of THF under argon with 1.46 g (7.21 mmol) of 4-(trifluoromethoxy)phenylisocyanate and stirred overnight at room temperature. The reaction mixture is filtered, the filtrate is concentrated by evaporation in a vacuum, and it is purified chromatographically.

Yield: 860 mg (62% of theory)
LC-MS (Method 4): $R_t$=2.41 min.
MS (ESI+): m/z=373 [M+H]+
$^1$H-NMR (300 MHz, DMSO-$d_6$): δ=8.98 (bs, 2H), 7.55 (m, 2H), 7.36 (s, 1H), 7.29 (m, 2H), 4.28 (q, 2H), 3.91 (s, 3H), 1.30 (t, 3H).

Example 4A

1-Methyl-4-[({[4-(trifluoromethoxy)phenyl]amino}carbonyl)amino]-1H-imidazole-2-carboxylic acid

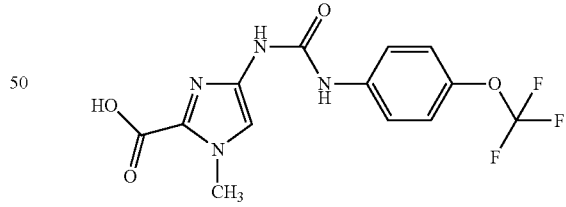

835 mg (2.13 mmol) of 1-methyl-4-[({[4-(trifluoromethoxy)phenyl]-amino}carbonyl)amino]-1H-imidazole-2-carboxylic acid ethyl ester (Example 3A) is suspended in 5 ml of ethanol and 12 ml of tetrahydrofuran. While being cooled with ice, 2 ml (25 mmol) of 50% aqueous sodium hydroxide solution is added. The reaction mixture is stirred overnight at room temperature and then made acidic with 1N hydrochloric acid while being cooled with ice. The solution is extracted with dichloromethane. The organic phase is concentrated by evaporation in a vacuum. The residue is purified by preparative HPLC.

Yield: 346 mg (44% of theory)

LC-MS (Method 3): $R_t$=1.62 min.

MS (ESI⁺): m/z=345 [M+H]⁺

¹H-NMR (400 MHz, DMSO-$d_6$): δ=9.33 (bs, 1H), 8.98 (bs, 1H), 7.55 (m, 2H), 7.30 (s, 1H), 7.28 (m, 2H), 3.90 (s, 3H).

Example 5A

1-Ethyl-4-[({[4-(trifluoromethoxy)phenyl]amino}carbonyl)amino]-1H-imidazole-2-carboxylic acid

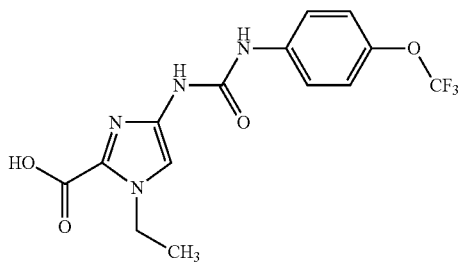 [SMILES: CCn1cc(NC(=O)Nc2ccc(OC(F)(F)F)cc2)nc1C(=O)O]

Production is done analogously to Example 4A.

Yield: 425 mg (91% of theory)

LC-MS (Method 4): $R_t$=1.94 min.

MS (ESI⁺): m/z=359 [M+H]⁺

¹H-NMR (300 MHz, DMSO-$d_6$): δ=10.3 (bs, 1H), 7.67 (m, 2H), 7.24 (s, 1H), 7.20 (m, 2H), 4.45 (q, 2H), 1.33 (t, 3H).

Example 6A

4-[({[4-(Difluoromethoxy)phenyl]amino}carbonyl)amino]-1-methyl-1H-imidazole-2-carboxylic acid

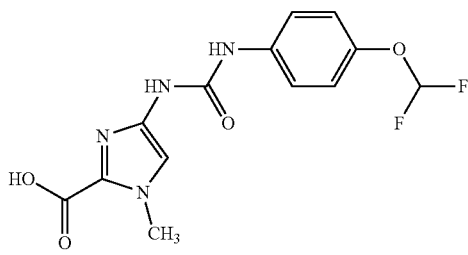 [SMILES: Cn1cc(NC(=O)Nc2ccc(OC(F)F)cc2)nc1C(=O)O]

Production is done analogously to Example 4A.

Yield: 964 mg (81% of theory)

HPLC (Method 5): $R_t$=3.57 min.

MS (ESI⁺): m/z=327 [M+H]⁺

¹H-NMR (400 MHz, CDCl₃): δ=8.9 (s, 1H), 8.8 (s, 1H), 7.5 (d, 2H), 7.3 (s, 2H), 7.1 (t, 1H), 7.09 (d, 2H), 3.9 (s, 3H).

Example 7A 1-(5-Methylpyridin-2-yl)piperazine

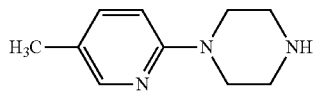

Stage 1

1-(tert-Butyloxycarbonyl)-4-(5-methylpyridin-2-yl)piperazine

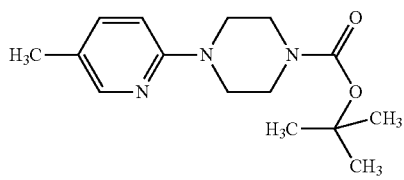 [SMILES: Cc1ccc(N2CCN(C(=O)OC(C)(C)C)CC2)nc1]

Under an argon atmosphere, 2.50 g (19.6 mmol) of 2-methyl-5-chloropyridine and 4.38 g (23.5 mmol) of N-(tert-butyloxycarbonyl)-piperazine are dissolved in 50 ml of absolute toluene. Then, 2.26 g (23.5 mmol) of sodium-tert-butylate, 0.37 g (0.59 mmol) of BINAP, and 0.36 g (0.39 mmol) of tris(dibenzylideneacetone)-dipalladium are added, and it is heated for 12 hours to 70° C. After cooling, the reaction mixture is mixed with diethyl ether, washed three times with saturated sodium chloride solution, dried on sodium sulfate, and solvent is removed in a vacuum. The residue is purified by flash chromatography (cyclohexane/ethyl acetate 9:1).

As an alternative, the coupling reaction can also be performed with use of palladium-(II)-acetate as a catalyst.

Yield: 5.27 g (97% of theory)

LC-MS (Method 3): $R_t$=1.26 min.

MS (ESI⁺): m/z=278 [M+H]⁺

¹H-NMR (300 MHz, CDCl₃): δ=8.02 (d, 1H), 7.34 (dd, 1H), 6.59 (d, 1H), 3.55 (m, 4H), 3.45 (m, 4H), 2.21 (s, 3H), 1.49 (s, 9H).

Stage 2

1-(5-Methylpyridin-2-yl)piperazine

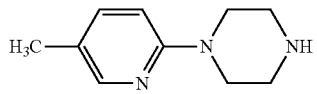

3.47 g (12.5 mmol) of 1-(tert-butyloxycarbonyl)-4-(5-methylpyridin-2-yl)piperazine is dissolved in 10 ml of dioxane and mixed with 31 ml (125 mmol) of hydrogen chloride in dioxane (4 mol). It is allowed to stir for 2 hours at room temperature. Then, it is concentrated by evaporation, the residue is alkalized with 1 M sodium hydroxide solution, and it is extracted several times with dichloromethane. The combined organic phases are dried on sodium sulfate, concentrated by evaporation, and dried in a vacuum.

As an alternative, the compound of Example 7A can also be isolated in the form of hydrochloride salt.

Yield: 2.18 g (98% of theory)
LC-MS (Method 4): $R_t$=0.38 min.
MS (ESI$^+$): m/z=177 [M+H]$^+$
$^1$H-NMR (300 MHz, CDCl$_3$): δ=8.02 (d, 1H), 7.32 (dd, 1H), 6.59 (d, 1H), 3.45 (m, 4H), 3.00 (m, 4H), 2.20 (s, 3H).

Example 8A

N-{1-Methyl-2-[(4-pyridin-2-yl-piperazin-1-yl)carbonyl]-1H-imidazol-4-yl}-N'-[4-(trifluoromethoxy)phenyl]urea

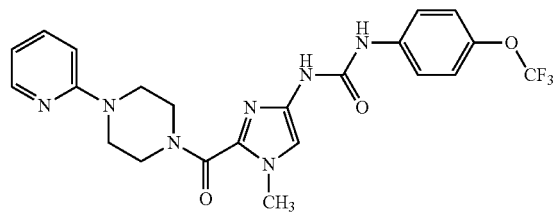 [SMILES: Cn1cc(NC(=O)Nc2ccc(OC(F)(F)F)cc2)nc1C(=O)N1CCN(c2ccccn2)CC1]

1.50 g (4.36 mmol) of the compound of Example 4A is dissolved in 30 ml of DMF and mixed with 1.82 g (5.66 mmol) of O-(benzotriazol-1-yl)-N,N,N',N'-tetramethyluronium tetrafluoroborate (TBTU) and 266 mg (2.18 mmol) of 4-dimethylaminopyridine. After adding 925 mg (5.66 mmol) of 1-(pyridin-2-yl)-piperazine, it is allowed to stir for 4 hours at room temperature. The reaction mixture is purified by RP-HPLC.

Yield: 1.79 g (83% of theory)
LC-MS (Method 1): $R_t$=1.83 min.
MS (ESI$^+$): m/z=490 [M+H]$^+$
$^1$H-NMR (400 MHz, DMSO-d$_6$): δ=8.89 (bs, 2H), 8.12 (d, 1H), 7.55 (m, 3H), 7.29 (m, 2H), 7.20 (s, 1H), 6.88 (d, 1H), 6.68 (dd, 1H), 4.02 (bs, 2H), 3.77 (s, 3H), 3.71 (bs, 2H), 3.58 (bs, 4H).

Example 9A

N-(1-Methyl-2-{[4-(5-methylpyridin-2-yl)piperazin-1-yl]carbonyl}-1H-imidazol-4-yl)-N'-[4-(trifluoromethoxy)phenyl]urea

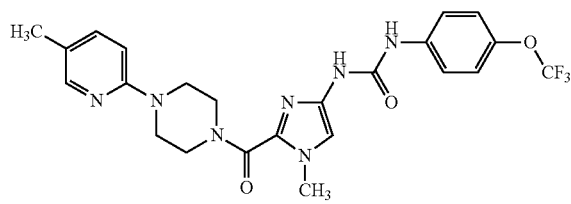 [SMILES: Cc1ccc(N2CCN(C(=O)c3nc(NC(=O)Nc4ccc(OC(F)(F)F)cc4)cn3C)CC2)nc1]

5.6 g (26.14 mmol) of the compound of Example 7A and 13.22 g (130.7 mmol) of N-methylmorpholine are added to a solution of 9.0 g (26.14 mmol) of the compound of Example 4A in 110 ml of ethyl acetate, and the reaction mixture is cooled to 0° C. 16.63 g (52.26 mmol) of propanephosphonic acid anhydride (T3P) is added to the reaction solution over 90 minutes, and the resulting suspension is stirred for another 10 minutes at this temperature. The reaction mixture is then heated over 60 minutes to 20° C. and stirred overnight at this temperature. Unreacted T3P is quenched by adding 45 ml of water, and the reaction mixture is stirred for another 10 minutes. Then, the phases are separated, and the organic phase is washed several times with water (3×45 ml), which is set at pH 5. The combined aqueous phases are washed once more with ethyl acetate, and the combined organic phases are washed twice with 45 ml of aqueous sodium bicarbonate solution, dried on sodium sulfate, and concentrated by evaporation. The crude product that is obtained is recrystallized from ethanol, after which the end product is obtained as a pale yellow solid.

Yield: 8.42 g (64% of theory)
LC-MS (Method 4): $R_t$=2.01 min.
MS (ESI$^+$): m/z=504 [M+H]$^+$
$^1$H-NMR (300 MHz, DMSO-d$_6$): δ=8.92 (bs, 2H), 7.99 (d, 1H), 7.54 (m, 2H), 7.42 (dd, 2H), 7.28 (m, 2H), 7.20 (s, 1H), 6.80 (d, 1H), 4.00 (bs, 2H), 3.77 (s, 3H), 3.72 (bs, 2H), 3.51 (bs, 4H), 2.16 (s, 3H).

Example 10A

N-(2-{[4-(5-Chloropyridin-2-yl)piperazin-1-yl]carbonyl}-1-ethyl-1H-imidazol-4-yl)-N'-[4-(trifluoromethoxy)phenyl]urea

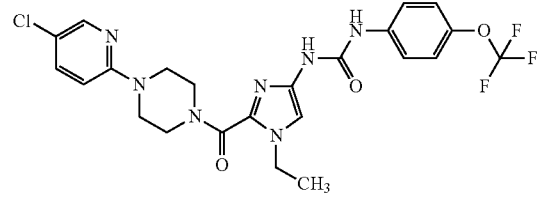 [SMILES: CCn1cc(NC(=O)Nc2ccc(OC(F)(F)F)cc2)nc1C(=O)N1CCN(c2ccc(Cl)cn2)CC1]

Production is done analogously to Example 9A from Example 5A.

Yield: 55 mg (68% of theory)
LC-MS (Method 4): $R_t$=2.76 min.
MS (ESI$^+$): m/z=538 [M+H]$^+$
$^1$H-NMR (300 MHz, DMSO-d$_6$): δ=8.97 (bs, 1H), 8.92 (bs, 1H), 8.14 (d, 1H), 7.65 (dd, 1H), 7.54 (m, 2H), 7.28 (m, 2H), 7.24 (s, 1H), 6.92 (d, 1H), 4.16 (q, 2H), 3.97 (bs, 2H), 3.72 (bs, 2H), 3.59 (bs, 4H), 1.32 (t, 3H).

Example 11A

N-(2-{[4-(4-Methoxyphenyl)piperazin-1-yl]carbonyl}-1-methyl-1H-imidazol-4-yl)-N'-[4-(trifluoromethoxy)phenyl]urea

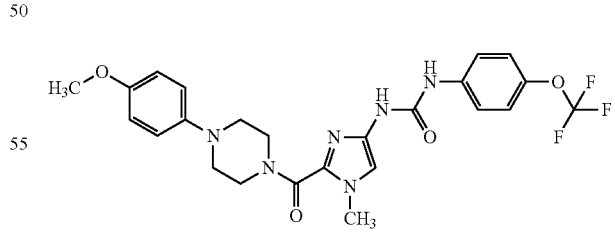

Production is done analogously to Example 9A from Example 4A.

Yield: 35 mg (58% of theory)
LC-MS (Method 3): $R_t$=2.24 min.
MS (ESI$^+$): m/z=519 [M+H]$^+$
$^1$H-NMR (400 MHz, DMSO-d$_6$): δ=8.89 (bs, 2H), 7.53 (m, 2H), 7.28 (m, 2H), 7.19 (s, 1H), 6.92 (m, 2H), 6.84 (m, 2H), 4.05 (bs, 2H), 3.75 (m, 5H), 3.69 (s, 3H), 3.08 (bs, 4H).

Example 12A

N-[4-(Difluoromethoxy)phenyl]-N'-(1-methyl-2-{[4-(5-methylpyridin-2-yl)piperazin-1-yl]-carbonyl}-1H-imidazol-4-yl)urea

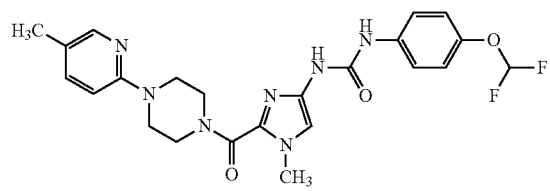 [SMILES: Cc1ccc(N2CCN(C(=O)c3nc(NC(=O)Nc4ccc(OC(F)F)cc4)cn3C)CC2)nc1]

Production is done analogously to Example 9A from Example 6A.

Yield: 17 mg (29% of theory)

LC-MS (Method 4): $R_t$=1.70 min.

MS (ESI$^+$): m/z=486 [M+H]$^+$ $^1$H-NMR (400 MHz, DMSO-d$_6$): δ=8.84 (bs, 1H), 8.77 (bs, 1H), 7.98 (d, 1H), 7.47 (m, 2H), 7.42 (dd, 1H), 7.18 (s, 1H), 7.11 (t, 1H), 7.10 (m, 2H), 6.80 (d, 1H), 4.01 (bs, 2H), 3.77 (s, 3H), 3.71 (bs, 2H), 3.50 (bs, 4H), 2.16 (s, 3H).

The examples of Table 1 are produced analogously to Example 8A.

TABLE 1

| Example No. | Structure | Molar Mass | MS (ESI) [M + H]$^+$ | LC-MS $R_t$ [min] (Method) | Starting Compound | Yield (% of Theory) |
|---|---|---|---|---|---|---|
| 13A | 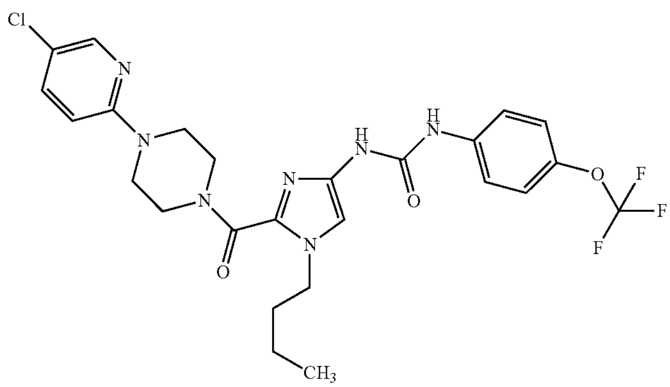 [SMILES: CCCCn1cc(NC(=O)Nc2ccc(OC(F)(F)F)cc2)nc1C(=O)N1CCN(c2ccc(Cl)cn2)CC1] | 565.981 | 566 | 2.94 (4) | Example 2A | 72 |
| 14A | 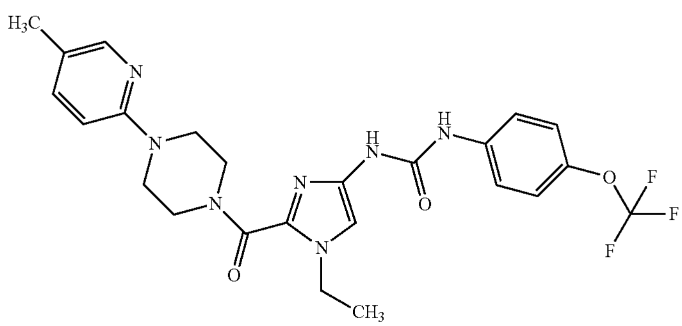 [SMILES: CCn1cc(NC(=O)Nc2ccc(OC(F)(F)F)cc2)nc1C(=O)N1CCN(c2ccc(C)cn2)CC1] | 517.509 | 518 | 1.94 (4) | Example 5A | 22 |
| 15A | 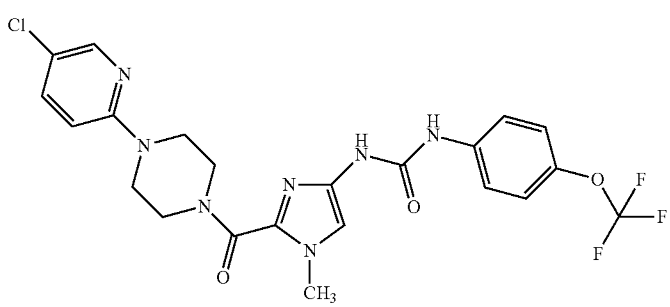 [SMILES: Cn1cc(NC(=O)Nc2ccc(OC(F)(F)F)cc2)nc1C(=O)N1CCN(c2ccc(Cl)cn2)CC1] | 523.901 | 524 | 2.67 (4) | Example 4A | 50 |

TABLE 1-continued

| Example No. | Structure | Molar Mass | MS (ESI) [M + H]+ | LC-MS R$_t$ [min] (Method) | Starting Compound | Yield (% of Theory) |
|---|---|---|---|---|---|---|
| 16A | 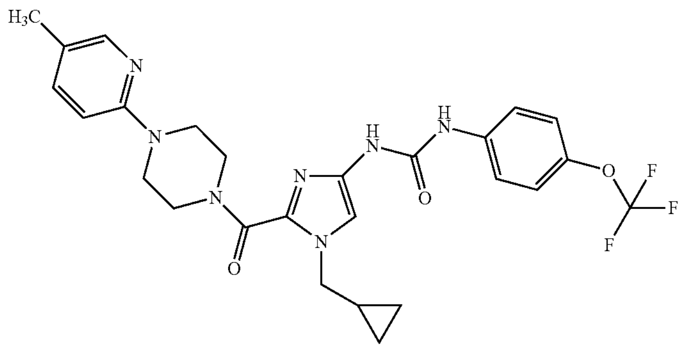 [SMILES: Cc1ccc(N2CCN(C(=O)c3nc(NC(=O)Nc4ccc(OC(F)(F)F)cc4)cn3CC3CC3)CC2)nc1] | 543.547 | 544 | 2.11 (4) | Example 1A | 59 |

Embodiments

Example 1

N-(1-Methyl-2-{[4-(5-methylpyridin-2-yl)piperazin-1-yl]-carbonyl}-1H-imidazol-4-yl)-N'-[4-trifluoromethoxyphenyl]urea dimesylate

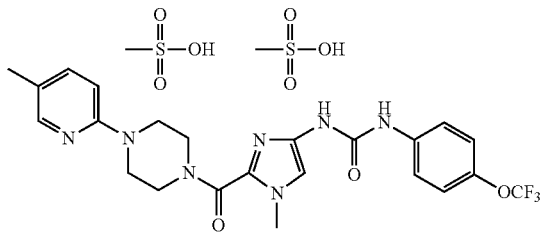

All operations are performed under a nitrogen-cover gas atmosphere. In a reaction vessel, 3,202 g of the compound of Example 9A (6.36 mol, 1 equivalent) is mixed with a mixture that consists of 15 l of THF and 1 l of water. The resulting suspension is slowly heated to 60° C. and then stirred for 30 minutes at this temperature. 1,252 g of methanesulfonic acid (13.03 mol, 2.05 eq.) is added to the yellowish solution that is formed and then is inoculated with N-(1-methyl-2-{[4-(5-methyl-pyridin-2-yl)piperazin-1-yl]-carbonyl}-1H-imidazol-4-yl)-N'-[4-trifluoromethoxyphenyl]urea dimesylate. Another 30 l of THF is added over 2 hours to the suspension that is produced from crystalline N-(1-methyl-2-{[4-(5-methylpyridin-2-yl)piperazin-1-yl]-carbonyl}-1H-imidazol-4-yl)-N'-[4-trifluoromethoxyphenyl]urea dimesylate. The suspension is slowly cooled to 20° C. and then stirred for another 12 hours at this temperature. The crystals that are formed are collected by vacuum filtration, and the reactor is flushed with THF and then n-heptane, whereby these organic phases are then used for washing the crystals. Finally, the crystals are dried on the filter under vacuum and under a stream of nitrogen. 4,262 g (yield: 96.4%, purity>99%) of the desired dimesylate salt is obtained.

$^1$H-NMR (400 MHz, DMSO-d$_6$): δ=9.07 (s, 1H), 8.98 (s, 1H), 7.99 (s, 1H), 7.92 (d, 1H), 7.56 (d, 2H), 7.41 (d, 1H), 7.33-7.24 (m, 3H), 4.18 (s, br., 2H), 3.92-3.69 (m, 9H), 2.43-2.39 (s, 6H), 2.25 (s, 3H).

The X-ray diffractogram depicted in FIG. 1 was recorded with use of a Rigaku MiniFlex powder-XRD spectrometer.

The compounds of Example 8A as well as Examples 10A to 15A can be converted analogously into the dimesylate salts.

Solubility Studies 20 mg of the compound of Example 1 as well as, for comparison, the citrate, maleate, sulfate and tartrate salts of the compound of Example 9A, as well as chloride salts of the compound of Example 9A, which were produced with 1, 2 and 4 equivalents of hydrochloric acid, as well as the free base, are weighed into HPLC glasses, which were equipped with a magnetic stirrer. 1 ml of H$_2$O each is added, and the HPLC glasses are sealed. The suspensions that are produced are stirred overnight at 25° C. To estimate the amount of dissolved substance, the suspensions are filtered via pipette microfilters, and the filtrates that are obtained are diluted 1:4 and analyzed by means of HPLC. The HPLC analysis was carried out on a Dionex Luna RP18 (100A)-column with the following dimensions: 5 μm 50×4.6 mm with use of an isocratic mixture of acetonitrile and H$_2$O+0.1% TFA in the ratio 3:7.

As a result of the solubility measurements, the values depicted in Table 2 below were determined.

TABLE 2

| Compound | Solubility [mg/ml] |
|---|---|
| Example 9A, Free Base | 0.004 |
| Example 9A, Citrate | 0.42 |
| Example 9A, Maleate | 0.12 |
| Example 9A, Sulfate | 0.18 |
| Example 9A, Tartrate | 0.72 |
| Example 9A, Chloride, 1 eq. | 0.19 |
| Example 9A, Chloride, 2 eq. | 0.07 |
| Example 9A, Chloride, 4 eq. | 0.11 |
| Example 1 | >9.70 |

These values clearly show the superior solubility of the salt of Example 1 in an aqueous medium relative to other salts of the compound of Example 9A.

Solubility Under Simulated Conditions in the Human Stomach

To determine the solubility under simulated conditions in the human stomach, suspensions of the salt of Example 1 as well as of the citrate and tartrate salts of Example 9A and the corresponding free base in aqueous sodium chloride solution (0.2% by weight), which was set at a pH of 1.2 with hydrochloric acid, are stirred for 5 hours. The samples were then treated as described above, and the amount of free base in solution is determined by means of HPLC. The corresponding values for the solubility under simulated conditions of the human stomach are depicted in Table 3 below.

TABLE 3

| Compound | Amount of Dissolved Free Base [mg/ml] |
|---|---|
| Example 9A, Citrate | 0.068 |
| Example 9A, Tartrate | 0.047 |
| Example 9A, Free Base | 0.065 |
| Example 1 | 0.103 |

This table clearly shows the considerably better solubility of the salts according to the invention under simulated conditions in the human stomach. In this connection, it is to be noted that after allowing the solution to stand for extended periods, the fresh occurrence of a suspension could be observed. It is to be expected that the latter originates from the formation of poorly soluble chloride salts of Example 9A. This observed formation of insoluble chloride salts was considered non-serious, however, since the latter—primarily when used in accordance with Example 1—has a delayed entry, and thus initially a metastable supersaturated solution is present. This is a further indication of the advantages that can be achieved with the use of the salts according to the invention for the production of medications.

Hygroscopy

By storing the salt of Example 1 in pure form at approximately 46% relative atmospheric humidity and 24° C., the hygroscopy of the salts according to the invention was measured. In this case, after a storage time of approximately 2 days, the salt of Example 1 showed a weight increase of less than 0.11%, which represents a hygroscopy that is acceptable for use in medications.

B. Evaluation of the Physiological Effectiveness

The in-vitro action of the compounds according to the invention on the replication of the HCMV (human cytomegalovirus) can be shown in the antiviral assay below:

HCMV Fluorescence Reduction Test

The test compounds are used as 50 millimolar (mM) solutions in dimethyl sulfoxide (DMSO). As reference compounds, e.g., Ganciclovir®, Foscarnet®, Cidofovir® or else the compound of Example 9A can be used. One day before the start of the test, $1.5 \times 10^4$ human foreskin fibroblasts (NHDF cells)/well are sowed in 200 µl of cell culture medium in the wells B2-G11 of 96-well plates (black with a translucent bottom). The wells at the edge position of each 96-well plate are filled only with 200 µl of medium to avoid edge effects. On the day of the test, the cell culture medium is suctioned off from the wells B2-G11 of each 96-well plate and replaced by 100 µl of virus suspension (multiplicity of infection (MOI): 0.1-0.2). The virus that is used is a recombinant HCMV, which has integrated an expression cassette for the green fluorescence protein (GFP) in the virus genome (HCMV AD 169 RV-HG, E. M. Borst, K. Wagner, A. Binz, B. Sodeik, and M. Messerle, 2008, *J. Virol.* 82: 2065-2078). After an incubation time of 2 hours at 37° C. and 5% $CO_2$, the virus inoculate is suctioned off, and all wells except for the wells in Column 3 are filled with 200 µl of cell culture medium. Column 2 is not further treated and serves as a virus control. The wells in Column 3 are filled in each case in double determination with 300 µl of test substance (diluted in cell culture medium). The concentration of the respective antiviral substance in Column 3 is ~ the 27× concentration of the $EC_{50}$ value that is expected in each case. The test substance in Column 3 is diluted in 8 steps 1:3 over the 96-well plate by in each case 100 µl of a column being transferred into the right column in each case—and being mixed there with the existing 200 µl of cell culture medium. In this way, three antiviral substances are tested in double determinations. The plates are incubated for 7 days at 37° C./5% $CO_2$. Then, all wells of a plate are washed 3× with PBS (phosphate buffered saline) and filled with 50 µl of PBS. Then, the GFP intensity of each well of a 96-well plate is determined by means of a fluorescence reading device (FluoBox; Bayer Technology Services GmbH; Filter settings: GFP, Ex 480 nm, Em 520 nm). The $EC_{50}$ of an anti-HCMV substance can be determined from the thus obtained measurement values:

$EC_{50}$ (GFP-RA)=Substance concentration in µM, which reduces the GFP fluorescence in infected cells by 50% in comparison to the untreated virus control.

Representative in-vitro active data for the compounds according to the invention are reproduced in Table 4:

TABLE 4

| Virus Strain | Example 9A $EC_{50}$ [µM] | Example 1 $EC_{50}$ [µM] | Ganciclovir $EC_{50}$ [µM] |
|---|---|---|---|
| AD169 RV-HG | 0.0015 | 0.0018 | 3.2 |

Embodiments of Pharmaceutical Compositions

The compounds according to the invention can be converted into pharmaceutical preparations as follows:

Tablet:

Composition:

100 mg of the compound of Example 1, 50 mg of lactose (monohydrate), 50 mg of corn starch (native), 10 mg of polyvinylpyrrolidone (PVP 25) (BASF Company, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% solution (m/m) of PVPs in water. After drying, the granulate is mixed with magnesium stearate for 5 minutes. This mixture is pressed with a common tablet press (format of the tablet, see above). A pressing force of 15 kN is used as a guide value for the pressing.

Suspension That Can be Administered Orally:

Composition:

1,000 mg of the compound of Example 1, 1,000 mg of ethanol (96%), 400 mg of Rhodigel (xanthan gum of the FMC Company, Pennsylvania, USA), and 99 g of water.

10 ml of oral suspension corresponds to an individual dose of 100 mg of the compound according to the invention.

Production:

The Rhodigel is suspended in ethanol, and the active ingredient is added to the suspension. While being stirred, the addition of water is carried out. It is stirred for approximately 6 hours until the swelling of the Rhodigel has ended.

Solution That Can be Administered Intravenously:

Composition:

5.53 g of the compound of Example 1, 1,000 g of water for injection purposes, which contains 10% (w/v) hydroxypropyl-β-cyclodextrin (Aldrich), and 985 mg of sodium acetate.

Production:

The compound according to the invention is dissolved in water while being stirred, and the pH of the solution is set with the sodium acetate at a pH of approximately 3.94. The solution is sterilized by filtration (pore diameter 0.22 µm) and decanted into heat-sterilized infusion flasks under aseptic conditions. The latter are sealed with infusion stoppers and flange caps.

The invention claimed is:

1. A salt of a compound of formula (I)

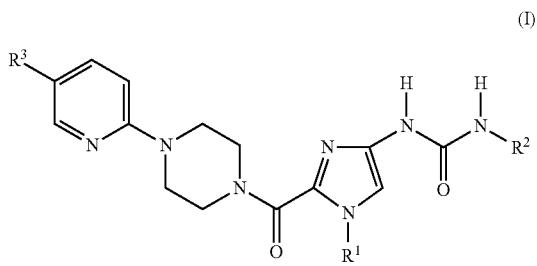

(I)

in which
R¹ stands for methyl, ethyl, butyl, or cyclopropylmethyl,
R² stands for phenyl, which phenyl is substituted with a substituent that is selected from the group consisting of trifluoromethoxy and difluoromethoxy, and
R³ stands for hydrogen, methyl, chlorine, methoxy, or trifluoromethyl,
with methanesulfonic acid
or a hydrate thereof.

2. A salt according to claim 1, which is a dimesylate salt.

3. A salt according to claim 1, which is of the following formula:

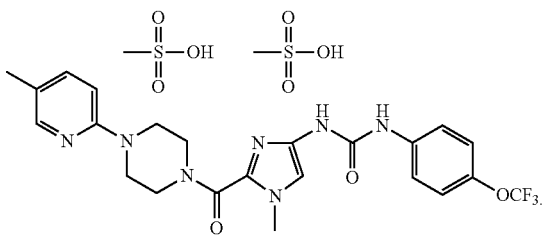

4. Crystalline N-(1-methyl-2-{[4-(5-methylpyridin-2-yl)piperazin-1-yl]-carbonyl}-1H-imidazol-4-yl)-N'-[4-trifluoromethoxyphenyl]urea dimesylate, which has a powder-XRD diffractogram with characteristic peaks at approximately 6.37, 11.77, 12.56, 17.17, 18.81, 20.34, 21.47, 23.04, and 35.46 degrees 2theta.

5. Crystalline N-(1-methyl-2-{[4-(5-methylpyridin-2-yl)piperazin-1-yl]-carbonyl}-1H-imidazol-4-yl)-N'-[4-trifluoromethoxyphenyl]urea dimesylate, which has a powder-XRD diffractogram as essentially depicted in FIG. 1.

6. A method for preparing a salt according to claim 1, comprising reacting a compound of Formula (I) or an acid salt of a compound of formula (I), which is not a salt of methanesulfonic acid, with methanesulfonic acid or a source of methanesulfonate ions in a solvent.

7. A pharmaceutical composition comprising a salt according to claim 1 in combination with at least one inert, non-toxic, pharmaceutically suitable adjuvant.

8. A pharmaceutical composition according to claim 7, comprising
5 to 12.5 mg/ml of a salt according to claim 1,
50 to 150 mg/ml of hydroxypropyl-β-cyclodextrin,
0.5 to 2.0 mg/ml of sodium acetate
as well as water and
optionally other pharmaceutically acceptable adjuvants.

9. A salt of a compound of formula (I) according to claim 1 with methanesulfonic acid.

10. A hydrate of a salt of a compound of formula (I) according to claim 1 with methanesulfonic acid.

11. A method for treating or preventing a viral infection by a member of Herpesviridae, comprising administering to a subject in need thereof an effective amount of a salt according to claim 1.

12. A method according to claim 11, which is for treating a viral infection by a member of Herpesviridae.

13. A method according to claim 11, which is for preventing a viral infection by a member of Herpesviridae.

14. A method according to claim 11, which is for treating a viral infection by a cytomegalovirus.

15. A method according to claim 11, which is for preventing a viral infection by a cytomegalovirus.

16. A method according to claim 11, which is for treating a viral infection by human cytomegalovirus.

17. A method according to claim 11, which is for preventing a viral infection by human cytomegalovirus.

18. A method for treating or preventing a viral infection by a member of Herpesviridae, comprising administering to a subject in need thereof an effective amount of a salt according to claim 3.

19. A method for treating or preventing a viral infection by a member of Herpesviridae, comprising administering to a subject in need thereof an effective amount of a salt according to claim 9.

20. A method for treating or preventing a viral infection by a member of Herpesviridae, comprising administering to a subject in need thereof an effective amount of a hydrate of a salt according to claim 10.

* * * * *